United States Patent [19]

Suga

[11] 4,092,122
[45] May 30, 1978

[54] CORROSION TESTING MACHINE

[76] Inventor: Nagaichi Suga, 32 Banshu-cho, Shinyuka-ku Tokyo, Japan

[21] Appl. No.: 791,886

[22] Filed: Apr. 28, 1977

[51] Int. Cl.² .......................... B08B 3/02; B08B 3/08; G01N 17/00; G01N 33/20
[52] U.S. Cl. .................................. 23/253 C; 134/102; 134/107; 134/153; 134/199
[58] Field of Search .......................... 23/253 C, 230 C; 134/95, 102, 105, 107, 108, 153, 199, 200

[56] References Cited

U.S. PATENT DOCUMENTS

| | | | |
|---|---|---|---|
| Re. 25,932 | 12/1965 | Neffenger | 23/253 C |
| 2,405,532 | 8/1946 | Todd | 23/253 C |
| 2,897,060 | 7/1959 | Dieman | 23/230 C X |
| 3,422,826 | 1/1969 | Ballard | 134/107 |

*Primary Examiner*—Robert M. Reese

[57] ABSTRACT

A corrosion testing machine having a cell within which specimens are to be subjected to corrosion testing; a spraying tower in the center of the cell and having means therein for producing a spray of a testing liquid extending in all directions from the top of the tower; a supporting column within the cell and rotatably mounted for rotation around the spraying tower; a motor coupled to the supporting column for rotating the column around the spraying tower; and an annular frame mounted on the supporting column around the spray tower having supports for supporting test pieces thereof in an inwardly and downwardly inclined position with the surfaces to be tested facing inwardly and upwardly toward the top of the spray tower. In the machine the spray of the testing liquid is evenly applied to the surface of the specimens to be tested.

6 Claims, 4 Drawing Figures

CORROSION TESTING MACHINE

This invention relates to a corrosion testing machine, and more particularly to a corrosion testing machine for testing the resistance of a coated metal surface to rust and corrosion.

BACKGROUND OF THE INVENTION AND PRIOR ART

It is conventional to treat the surface of a metal by plating, painting or oxidation to make the metal resistant to rust and corrosion. In order to study the effect of these treatments, an etching or a corrosion acceleration tester has been used.

The Japanese Industrial Standard (JIS) define several corrosion acceleration tests such as, for example, a brine spraying method, a CASS testing method and a wet testing method, which are effective for testing with respect to a single corrosion factor.

The requisites for a good corrosion acceleration testing machine can be summarized as follows.

a. All of the test pieces disposed in the cell for the treating liquid must be kept under the same conditions.

b. The test performed by the testing machine must be reproducible.

c. The testing machine must produce a testing condition having a certain relation to an outdoor exposure test.

Unfortunately, conventional corrosion acceleration testing machines have failed to satisfy all of these requisites.

In conventional brine spraying testing machines and CASS (i.e. copper-accelerated acetic acid salt spray) testing machines, 30 to 50 test pieces each having a width of 70 mm and a height of 150 mm are disposed and fixed in a cell at an inclination of 15° or 30°.

Then, brine or CASS liquid is sprayed from a spraying tower disposed at the center of the bath, as shown in FIG. 1, or a nozzle located at one side of the bath onto the test pieces, as shown in FIG. 2. According to the JIS regulations, the rate of spray is typically 1 to 2 cc/hr. for every 80 cm$^2$ of the surface of the specimens. This wide range of the amount of spray inevitably causes local fluctuation of corrosion acceleration. The flow of the atomized brine, as well as the particle size of the brine, inconveniently fluctuate depending on the condition of the nozzle, which reduces the reliability and reproducibility of the test.

In a conventional tester as described above, the test pieces are kept stationary. When they are thus held, it is difficult to obtain an even distribution of the spray, regardless of how the spraying action itself is improved. It is true that conventional spraying machines have been improved to avoid local thickening and thinning of the spray. The adoption of a centrally disposed spraying tower, for example, provides a more even distribution of the spray over the test pieces, as compared with a nozzle system employing a nozzle located at one side of the container. However, even a centrally disposed spraying tower cannot satisfactorily apply the testing liquid to the test pieces, although it is the best method up to now. This limitation is entirely attributable to the stationary or unmovable positioning of the test pieces.

OBJECTS AND BRIEF SUMMARY OF THE INVENTION

It is a first object of the present invention to provide a corrosion tester which functions to satisfactorily meet the requisites listed above.

It is a further object of the present invention to provide a corrosion tester which overcomes the above described drawbacks of the prior art testing machines.

The corrosion testing machine of the present invention has an annular supporting frame adapted to carry a plurality of test pieces. The annular suporting frame is adapted to be rotated around a centrally disposed spraying tower so that the brine sprayed from the spraying tower will be applied evenly over the test pieces.

BRIEF DESCRIPTION OF THE FIGURES

These and other objects, as well as advantageous features of the invention will become clear from the following description of a preferred embodiment taken in conjunction with the attached drawings.

DETAILED DESCRIPTION OF THE INVENTION

Figure 1:
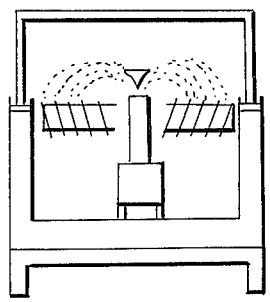
FIGS. 1 and 2 are schematic sectional views of conventional corrosion testing machines.
Figure 2:
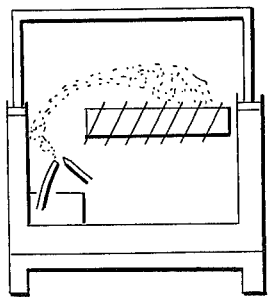
Figure 4:
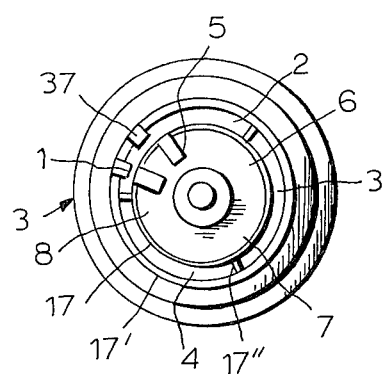
FIG. 4 is a plan view, on a reduced scale, of the testing machine of FIG. 3.
Figure 3:
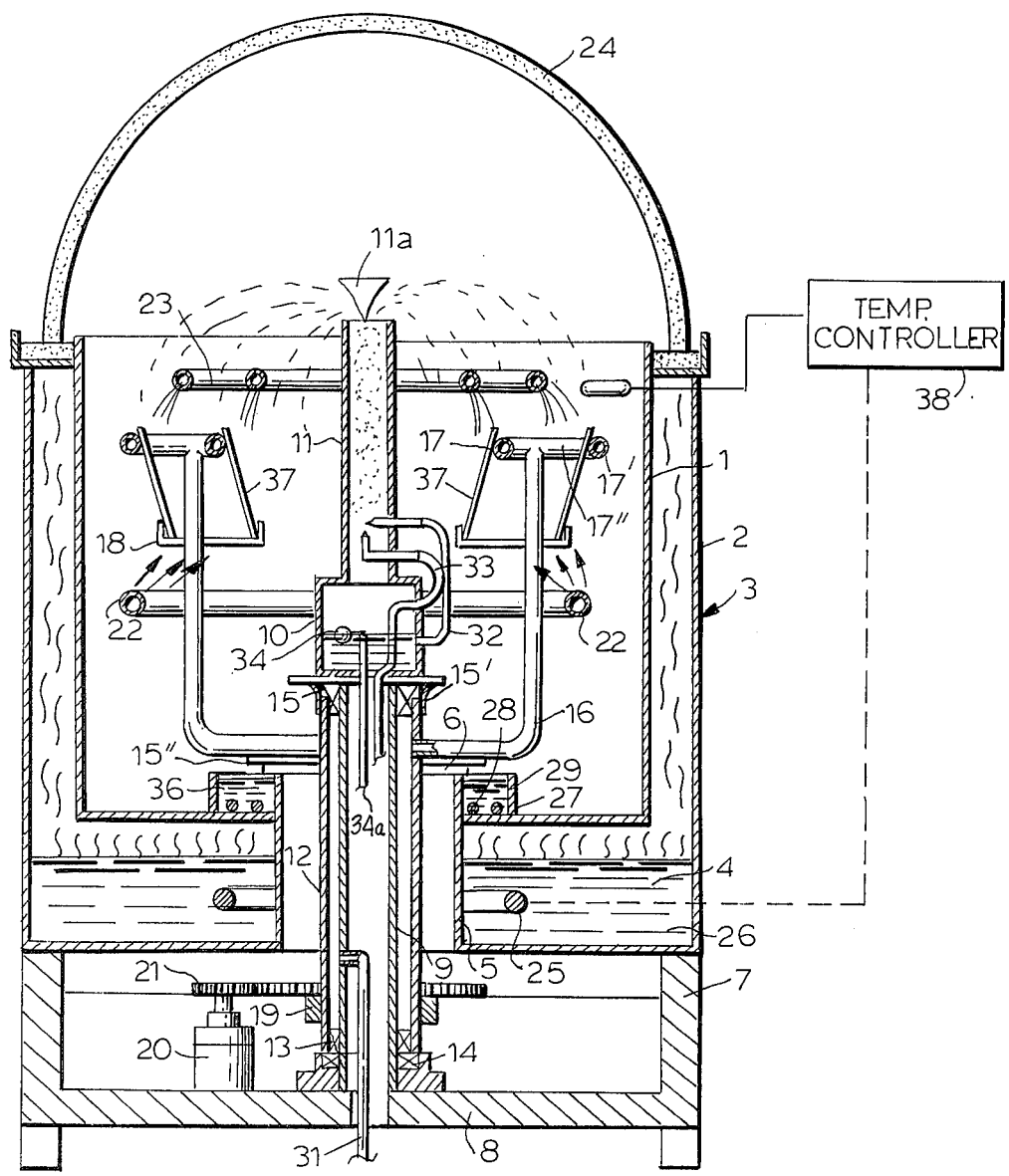
FIG. 3 is a sectional view of a testing machine according to the present invention.

Referring to FIG. 3, an airtight cell 3 consists of an inner cup-shaped sleeve 1 and an outer cup-shaped sleeve 2 of a corrosion-resistant material such as hard vinyl chloride. A cylinder 5 is disposed at the center of the bottom portion 4 of the cell 3 and projects from the bottom of sleeve 2 upwardly into the lower portion of inner sleeve 1. A supporting plate 6 within the sleeve 1 is mounted on a hollow rotary shaft 12 which is within the cylinder 5. The cell 3 is mounted on a base frame 7 having a supporting plate 8 on the bottom thereof at the center of which is provided a hollow stationary shaft 9. The stationary shaft 9 extends upwardly within the shaft 12 through the cylinder 5 and the supporting plate 6 carried by the rotary shaft 12 into the cell 3. The stationary shaft 9 carries at its upper end a brine container 10 having an upper cover with a central opening from the periphery of which protrudes a tubular spraying tower 11. The rotary shaft 12 concentrically surrounds the stationary shaft 9 and is supported by a bearing 13 for free rotation relative to the stationary shaft 9. The weight of the rotary shaft 12 is born by a thrust bearing 14 provided on the supporting plate 8. The upper portion of the rotary shaft 12 is supported on the stationary shaft 9 by means of a bearing 15 interposed between the shaft 9 and shaft 12. A sealing member 15' is provided at the upper end of the rotary shaft 12. A sealing member 15" secured to the cylinder 5 is effective to seal the cavity between the cylinder 5 and the rotary shaft 12, being in sealing engagement with the lower surface of the supporting plate 6. The sealing members 15' and 15" may be conventional V rings or water seals. A plurality of L-shaped hollow columns 16 are secured at intervals around the periphery of the portion of the rotary shaft 12 projecting above the supporting plate 6 and are in communication with the interior of shaft 12. A double annular frame 17, 17' consisting of hollow pipes is secured to the upper ends of the hollow columns 16. As will be seen from FIG. 4, the inner and outer annular pipes 17 and 17' constituting the annular frame are connected to each other by interconnecting pieces 17" which are at the tops of the columns 16, the rotary sleeve 12, columns 16, annular frame 17, 17' and the interconnecting pieces 17" are in fluid communication with one another for passing liquid therethrough.

Receiving plates 18 are secured to the hollow supporting columns at a position below and radially inwardly of the annular frames 17, 17'. A gear 19 is fixed on the lower portion of the rotary sleeve 12, and a gear 21 on a motor 20 supported by the supporting plate 8 is meshed with gear 19.

Within the cell 3 is a hollow ring 22 positioned radially outwardly of the supporting columns 16, i.e., at a position outside of a cylinder defined by the rotation of the rotary supporting columns 16 and at a height between the receiving plate 18 and the bottom 4 of the cell 3. The hollow ring 22 is in communication with a hot air cell provided at the outside of the cell 3.

A double ring 23 having a radius smaller than that of the annular frame 17, 17' is provided above the frame 17, 17' and is in communication with a source of liquid.

The annular frame 17, 17' is provided with a plurality of small apertures directed obliquely downwardly and radially inwardly, while the hollow ring 22 is provided with small apertures directed obliquely upwardly and radially inwardly. The double ring 23 is also provided with a plurality of apertures directed radially outwardly and obliquely downwardly. These apertures are at suitable uniform intervals around the respective members.

A cover 24 in the form of a double shell fitted with a heat insulating material is fitted on the cell 3 for closing the opening of the cell 3 in an airtight manner.

The space between the lower portions of the inner and the outer sleeves 1 and 2 constitutes a container for water 26 in which is a heater 25. A water pan 36 is positioned within the cell 3 and is constituted by an annular wall 27 on the bottom of the inner cylinder 1 around the cylinder 5 and in which are a heater 28 and a bubble nozzle 29. The pan 36 is adapted to be charged with water. A water supply pipe 31 extends upwardly through the supporting plate 8 into the lower portion of the stationary shaft 9 and then laterally through the wall of shaft 9 and opens into the space between the stationary shaft 9 and the rotary shaft 12.

Nozzles 32 and 33 for air and brine, respectively, are provided in tower 11, the brine nozzle being connected to container 10. A float 34 is connected to the end of brine supply pipe 34a for adjusting the brine level respectively.

The test pieces 37 are held in the inclined position, being supported at their lower ends by the receiving plates 18 and having the upper back surface thereof resting on the annular frames 17 and 17', and the treated surfaces are directed radially inwardly.

In operation, the underwater heater 25 is energized to generate steam which fills the space between the outer sleeve 2 and the inner sleeve 1 to heat the latter from outside thereof.

The adjustment of the temperature within the inner sleeve is performed by a temperature controller 38 having a sensor projecting into the inner sleeve 1, and which is effective to control the heater 25 in response to the temperature within the inner sleeve 1, thereby to carry out the required temperature control.

Air supplied to the nozzles 32 aspirates brine through nozzle 33 to produce a spray of the brine directed up tower 11, while the motor 20 is energized to rotate the rotary shaft 12 and, accordingly, the supporting columns 16, so that the spray of the brine deflected by deflector 11a at the tower 11 is applied evenly over the test pieces 37.

The following table shows the effect of the spray, based on the results of an experiment. The points at which the spraying density was checked are shown by the circled numbers in FIG. 4.

| Points at which spray observed | 1 | 2 | 3 | 4 | 5 | 6 | 7 | 8 |
|---|---|---|---|---|---|---|---|---|
| Amounts of Spray cc/hr | 1.4 | 1.5 | 1.6 | 1.4 | 1.3 | 1.4 | 1.4 | 1.3 |

Thus, it was observed that the spraying density, i.e., the amount of the spray, is within the range of 1.3 to 1.6 cc/hr over the entire area of the spray, which is much more uniform than that obtained in a conventional corrosion testing machine. Thus, the fluctuation of the spray density is greatly reduced so as to provide a much more even distribution of the spray over the test pieces, which in turn produces an enhanced reliability and reproducibility of the corrosion test.

There is another factor which affects the generation of corrosion, i.e., the size of the particles of the spray. The rate of generation of corrosion would be different, even where the amount of spray received by the test pieces is equal, if there were a difference in the size of the particles received by the different test pieces.

The following table shows the results of a test carried out to investigate the rate of generation of rust for 5 test pieces, for the conventional nozzle spraying methods, the conventional spraying tower system and for the spraying system of the invention. In the table, the values are represented by rating numbers.

| Test Piece | 1 | 2 | 3 | 4 | 5 |
|---|---|---|---|---|---|
| Conventional nozzle system | 5 | 3 | 3 | 2 | 2 |
| Conventional spraying system | 5 | 4 | 4 | 3 | 2 |
| System of invention | 4 | 4 | 4 | 4–3 | 4–3 |

Although the brine spraying corrosion testing machines, as well as CASS testing machines and wet testing machines are effective for a single corrosion factor, they do not always exhibit a constant conformity with actual outdoor corrosion. In other words, they cannot exactly reproduce outdoor corrosion conditions. Thus, a surface treatment judged to have a high corrosion-resistance as a result of a corrosion test may be corroded sooner in actual outdoor conditions than it was in the corrosion test. This is because of various corrosion factors existing in outdoor conditions which are related with each other in a complicated manner. In addition, the material is subjected to various conditions such as moistening, dew and drying. The repeated cycle of moistening, dew and drying under the influence of natural corrosion factors, i.e., a repeated oxidation and reduction cycle, greatly affects the corrosive deterioration.

In this connection, it is a great advantage that the corrosion testing machine of the present invention can perform, in addition to the above described uniform application of the spray, a cycle of treatment consisting of rinsing, drying, cooling and moistening, and drying.

The cooling of the test pieces is performed in the following way.

Cold water is fed through the water feeding pipe 31 and supplied to the annular frame 17, 17', through the space between the stationary shaft 9 and the rotary shaft 12 and then through the hollow supporting columns 16, being jetted through the small apertures formed in the annular frame 17, 17'. The jetted cold water colides with the back surface of the test pieces 37 to cool them.

For moistening of the test pieces, the water in the pan 36 is heated by the heater 28. The temperature of the water is controlled by a temperature controller (not shown) similar to temperature controller 38. Air is jetted from the bubble nozzle 29 which is connected to a compressor (not shown), the air from which is passed through an air saturating device (not shown) to saturate it with water. The saturated air is ejected from the nozzle 29 in the pan 36, to form bubbles, whereby the air in the inner sleeve 1 is kept at a high humidity.

The rinsing and drying of the test pieces are performed in the following manner.

The water supplied to the double ring 23 is ejected therefrom through the apertures and is sprayed onto the surface of the test pieces 37. Then hot air from a hot air cell (not shown) or ambient air is supplied to the inside of the cell 3 through the hollow ring 22 to dry the test pices.

As has been described, the corrosion testing machine of the invention is capable of applying a uniform spray of brine or CASS liquid onto the test pices, thanks to the rotation of the test pieces around a spraying tower for effecting the spray, thus avoiding a fluctuation in the density of the spray or lack of uniformity of spray particle size which can not be avoided in the conventional testing machines.

In addition, the hollow rotary sleeve makes possible the supply of water to the annular frame, through the supporting columns, which provides means for cooling the test pieces from their back surfaces.

The water pan formed at the bottom of the inner sleeve conveniently provides, in combination with the bubble nozzle therein for jetting air into the water contained in the pan, means for suitably moistening the inside of the cell.

The hollow double ring conveniently constitutes a water spraying nozzle for rinsing the test pieces.

Drying means are constituted by the hollow ring disposed within the cell and adapted to apply hot air to dry the test pieces.

These means are adapted to be operated in sequence to faithfully reproduce outdoor conditions. Namely, at first the brine spray is produced, then the specimens are rinsed, then dried by hot or ambient air, and cooled. The test pieces are moistened to simulate formation of dew on the surfaces of the test pieces and then drying is effected. It will be understood that this cycle of operation, reproducing outdoor conditions, provides a test which has a high degree of conformity with natural outdoor corrosion conditions.

What is claimed is:

1. A corrosion testing machine comprising: a cell within which specimens are to be subjected to corrosion testing; a spraying tower in the center of said cell and having means therein for producing a spray of a testing liquid extending in all directions from the top of the tower; a supporting column within said cell and rotatably mounted for rotation around said spraying tower; means coupled to said supporting column for rotating said column around said spraying tower; and an annular frame means mounted on said supporting column around said spray tower having means for supporting test pieces thereon in an inwardly and downwardly inclined position with the surfaces to be tested facing inwardly and upwardly toward the top of said spray tower, whereby the spray of the testing liquid is evenly applied to the surface of the specimens to be tested.

2. A corrosion testing machine as claimed in claim 1 in which said supporting column and annular frame means are hollow, and said annular frame means has a plurality of openings therein directed obliquely downwardly and inwardly substantially along the back surfaces of the specimens supported thereby, and further comprising means for supplying a cooling liquid to said supporting column, and a water vaporizing means in the interior of said cell, whereby water vapor can be generated in the cell to deposit dew on the surfaces of the specimens to be tested when the back surfaces of the specimens are cooled by flowing cooling water thereover.

3. A corrosion testing machine as claimed in claim 2 in which said water vaporizing means is a water pan in the bottom of said cell having heater means therein and bubble nozzle means therein for bubbling air through the water in the pan.

4. A corrosion testing machine as claimed in claim 1 further comprising a hollow ring within said cell and positioned above said annular frame and having a plurality of apertures therein directed downwardly toward the specimens supported by said frame means, and means for supplying said hollow ring with a rinsing liquid, whereby the specimens can have the surfaces to be tested rinsed.

5. A corrosion testing machine as claimed in claim 1 further comprising an annular tube in the shape of a ring around the inside of said cell below said frame means and outside the cylinder defined by the rotation of said supporting column, said tube having apertures therein directed upwardly toward the specimens held by said frame means, and means for supplying said annular tube with a drying gas, whereby the specimens can be dried by drying gas jetted from said annular tube.

6. A corrosion testing machine as claimed in claim 1 wherein said cell has hollow walls and a hollow bottom, and a heater means within said hollow bottom, whereby said bottom can have a body of liquid placed therein and heated for heating the interior of the cell.

* * * * *